United States Patent [19]

Scholz

[11] Patent Number: 4,836,186
[45] Date of Patent: Jun. 6, 1989

[54] BODY COMPRESSION DEVICE FOR PATIENTS UNDER FLUOROSCOPIC EXAMINATION

[76] Inventor: Francis J. Scholz, 32 Grand Hill Rd., Dover, Mass. 02030

[21] Appl. No.: 3,756

[22] Filed: Jan. 16, 1987

[51] Int. Cl.$^4$ .............................................. A61B 1/00
[52] U.S. Cl. ..................................... 128/897; 128/20; 128/60
[58] Field of Search ................... 128/1 R, 3, 20, 24 R, 128/24.2, 44, 60, 61, 62

[56] References Cited

U.S. PATENT DOCUMENTS

| | | | |
|---|---|---|---|
| 2,057,190 | 10/1936 | Haynos | 128/62 R |
| 2,450,935 | 10/1948 | Carr | 128/1 R |
| 3,677,262 | 7/1972 | Zukowski | 128/6 |
| 3,728,739 | 4/1973 | Semp | 128/1 UX |
| 3,866,597 | 2/1975 | Boxer | 128/1 R |
| 3,987,787 | 10/1976 | Boxer | 128/1 R |
| 4,041,931 | 8/1977 | Elliott et al. | 128/1 R |
| 4,181,123 | 1/1980 | Crosby | 128/6 |
| 4,202,349 | 5/1980 | Jones | 128/1 R X |
| 4,421,107 | 12/1983 | Estes et al. | 128/20 |
| 4,483,328 | 11/1984 | Wolocko | 128/61 X |

Primary Examiner—William H. Grieb
Attorney, Agent, or Firm—Doanld W. Meeker

[57] ABSTRACT

A hand held device allows force to be exerted on a body of a patient without causing muscle fatigue of the hand. Preferably the device is made of a radiolucent material. This device is particularly useful when used to manipulate or depress the abdomen to displace one bowel loop away from another so that tumors or other abnormalities of the gastrointestinal tract can be visualized during fluoroscopy. The device has a lever arm with a wrist cuff at an end of the lever arm and a handle both extending from the lever arm with a compression cone at the end of the lever arm opposite the wrist cuff. The user grips the handle with the wrist cuff resting across the dorsum of the wrist. Pressure is exerted on the abdomen by the cone by volar flexion of the wrist. Additional pressure and sensitivity are obtained by the use of a finger tab extending from the lever arm at a position between the handle and the cone. A thumb rest rib on the handle also improves sensitivity.

18 Claims, 1 Drawing Sheet

BODY COMPRESSION DEVICE FOR PATIENTS UNDER FLUOROSCOPIC EXAMINATION

BACKGROUND OF THE INVENTION

1. Technical Field

The present invention relates to a hand held device for exerting force and in particular to a compression device to be used by a radiologist during fluoroscopic examinations to flatten portions of the abdomen and to displace one bowel loop away from another so that tumors and other abnormalities of the gastrointestinal tract can be visualized.

2. Background Art

Compression of the abdomen during fluoroscopic examinations of the stomach and colon is a required manuever in most examinations. Compression of the abdomen allows the radiologist to displace loops overlying the region of interest, to press on areas of interest to accentuate the contrast between a lesion and the barium used for the examination, and to improve visualization by compressing and decreasing the amount of tissue through which the x-ray passes. Compression can be accomplished by a compression cone rigidly affixed to an x-ray machine, by using only the lead gloved hand directly, or by a hand held device. Palpation and compression by the gloved hand alone is discouraged by most radiologists because the lead stops many but not all x-rays in the primary beam in the area being fluoroscoped. The lead glove will stop all of the scatter radiation produced near the primary beam of x-ray. For this reason, manual compression devices are favored when compression is used.

Many manual devices have been used to permit better control and sensitivity of compression. Devices range from wooden kitchen spoons to commercial wood, plastic, and rubber balloon devices. All manual compression devices require use of a lead glove to protect the hand from direct and scattered radiation. Currently the devices which are available are cumbersome to grasp with a lead glove. All cause muscle fatigue of the hand because the fingers and thumb of the hand are required to grasp them. Compressive pressures exerted by the hand, wrist, and forearm tend to counteract and increase the grasping work being done by the fingers with all other devices.

DISCLOSURE OF THE INVENTION

This device is intended generally to permit the exertion of force by a hand held device upon a workpiece with minimal fatigue to the hand of the user.

In particular, this device is intended to permit compression of the abdomen, the workpiece, by a compression cone during fluoroscopy with the minimum amount of use of the small muscles of the hand and wrist and the maximum use of the major muscles of the wrist and forearm. It utilizes the principle of the lever with the dorsal surface of the wrist being one lever point and the volar or palmer surface of the distal palm which grips a handle as the second lever point. Using simultaneous downward pressure with the palm and upward pressure with the wrist, pressure is transmitted to the third point of the lever which presses on the desired portion of the abdomen. This complex sounding combination of motions is accomplished by simple volar flexion of the wrist. The unique design links the forces of the palm and wrist and permits fatigue-less compression which can be easily controlled with the hand while wearing a lead shielded fluoroscopic glove. Use of the finger muscles is optional for additional pressure or for added sense of control.

The device permits effective manual compression with the minimal possible radiation to the hand. The lever action compression is mechanically more efficient than compression delivered by any device grasped by the fingers. Because of this, a longer distance can be created between the compression point which is being x-rayed by fluoroscopy and the lead gloved hand bearing the device. To achieve equal compression, the hand with any finger and thumb grasped device must come closer to the compression point.

The design and choice of material of the compression cone minimizes the visualization of the cone on an x-ray film.

A thumb rest rib gives improved control of the device.

BRIEF DESCRIPTION OF THE DRAWINGS

These and other objects and advantages will be described with reference to the accompanying drawings, which are furnished merely by way of illustration, but not in limitation of the invention, and in which drawings.

BEST MODE FOR CARRYING OUT THE INVENTION

Figure 1:
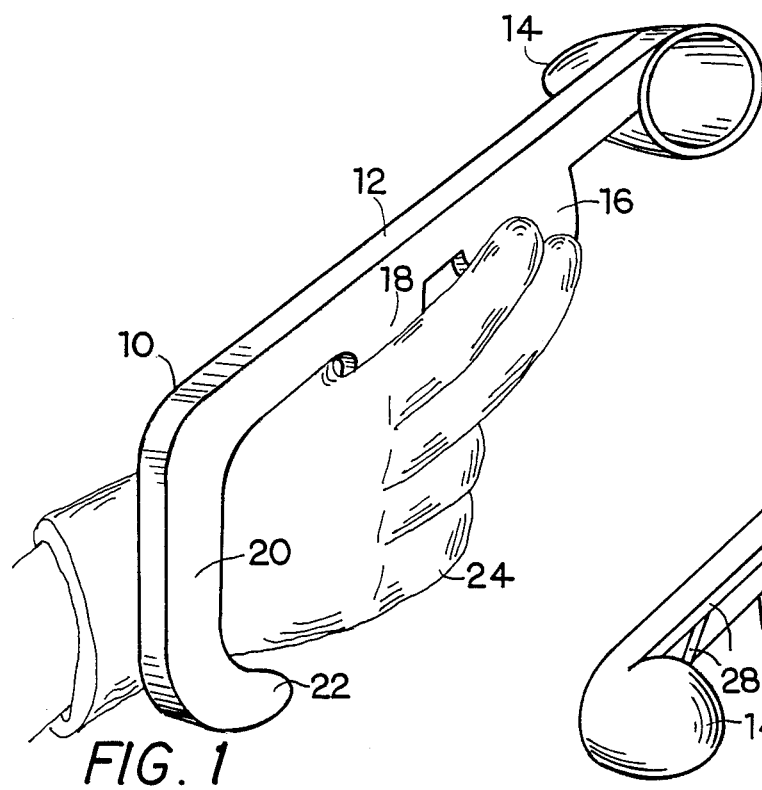
FIG. 1 is a perspective view of the invention held in a user's gloved hand.
Figure 2:
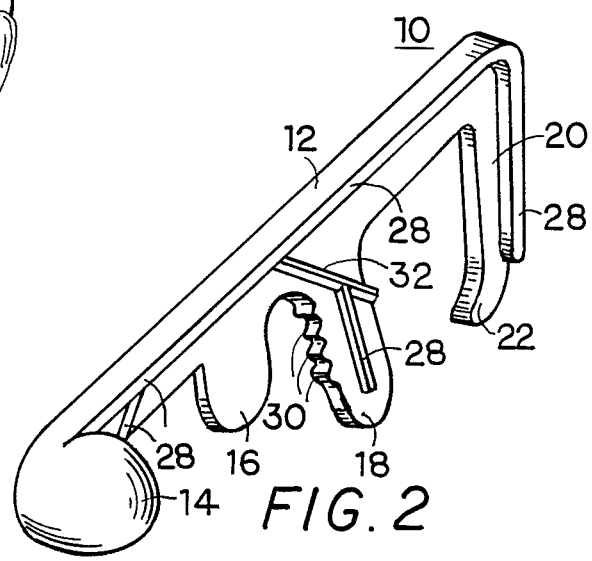
FIG. 2 is a perspective view of an opposite side of the invention from that shown in FIG. 1.
Figure 3:
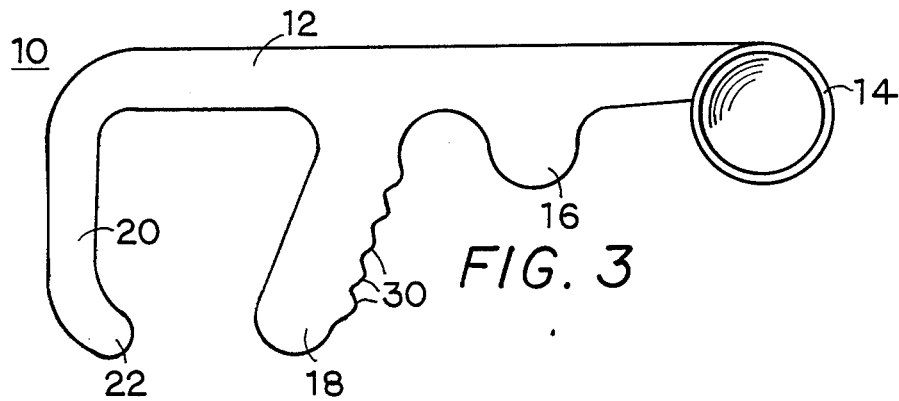
FIG. 3 is a side elevational view of the invention.
Figure 4:
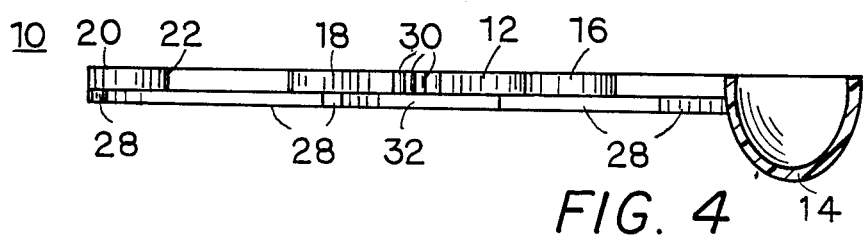
FIG. 4 is a bottom view of the invention in partial section.

The device 10 may be made to be used by the right or left hand. The figures disclose a right handed device. A right handed model can be used with moderate efficiency on the left hand if necessary. Alternatively, a left handed device may be made using a mirror image of the right handed device. It is understood that the following is applicable to both the right handed and left handed device. The device 10 is preferably made of a material such as plastic which allows the device 10 to be light weight, radioluscent to x-rays and sturdy enough to remain rigid when pressure is applied.

Referring to the figures, the preferred embodiment of the body compression device 10 has a lever arm 12 with wrist cuff 20 extending from the rearward end of the lever arm 12 and compression cone 14 positioned at the forward end of the lever arm 12. Palm grip handle 18 extends from the lever arm 12 in the same direction as the wrist cuff 20. The handle 18 is positioned between the wrist cuff 20 and the compression cone 14 such that the lead gloved hand 24 of the examiner can be inserted between the handle 18 and the wrist cuff 20 with the palm and fingers positioned to allow gripping of the handle 18 with the dorsum of the wrist resting against the wrist cuff 20. This positioning of the handle 18 relative to the wrist cuff 20, along with the hook end 22 of the wrist cuff 20, permits the device 10 to remain snugly in the lead gloved hand 24 without requiring pressure to grasp and hold the device 10 and yet the device 10 is not easily dislodged during an examination. For improved gripping, the handle 18 is provided with a non-slip gripping edge 30. To apply force for compression of the abdomen during fluoroscopy, simulatneous downward pressure is applied by the hand on the handle 18 and upward pressure is applied by the wrist on the wrist cuff 20. This transmits the force via the lever arm 12 to the cone 14. The length of the lever arm 12 can be varied at time of manufacture to vary the lever compression efficiency. The pressures required are accomplished by simple volar flexion of the wrist. A rotary component can be added to the compressive force being exerted on the abdomen by the interaction of the handle 18, wrist cuff 20 and the forearm of the examiner by rotating the forearm.

To allow additional pressure to be exerted on the abdomen by the cone 14 and to allow greater sensitivity for the examiner, a finger tab 16 extends from the lever arm 12 in the same direction as the handle 18. The tab 16 is positioned foward of the handle 18.

Thumb rest rib 32, which is an elongated protrusion on the handle 18, also improves the control of the device.

Reinforcing rib 28, which is an elongated protrusion on the planar surface 26 formed by the lever arm 12 handle 18 and wrist cuff 20 improves the strength of the device 10.

The compression cone 14 is hollow with walls that gradually taper to the rounded apex of the cone 14. Thus the x-ray beam will not pass through more than twice the thickness of the walls.

A non-opague marker 15 of a desired specific dimension can be inserted into the cone 14 during or after manufacture of the device 10 to allow measurement of abnormal lesions of the gastrointestinal tract.

It is understtod that the preceeding description is given merely by way of illustration and not in limitation of the invention and that various modifications may be made hereto without departing from the spirit of the invention as claimed.

I claim:

1. A device held in a hand of a user and extending over a wrist, the device being used for exerting force on a body of a patient wherein the device comprises:
    a lever arm having a forward end and a rearward end;
    a handle extending from the lever arm at a position between the forward end and the rearward end;
    a wrist cuff extending from the lever arm in the same direction as the handle, the wrist cuff being positioned closer to the rearward end than the handle and;
    a work element positioned at the forward end, the work element exerting force on a body of a patient.

2. The invention of claim 1 wherein the device further comprises;
    a finger tab extending from the lever arm in the same direction as the handle, the tab being located forward of the handle.

3. The invention of claim 1 wherein the device further comprises;
    a planar surface of the lever arm and the handle and;
    a thumb rest rib comprising an elongated protrusion extending substantially perpendicularly from the planar surface.

4. The invention of claim 1 wherein the device further comprises;
    a planar surface of the lever arm, wrist cuff and handle and;
    a reinforcing rib comprising an elongated protrusion on the planar surface.

5. The invention of claim 1 wherein the wrist cuff further comprises a hook end at the end of the wrist cuff not adjacent to the lever arm.

6. The invention of claim 1 wherein the device is a body compression device and the work element is a compression cone.

7. The invention of claim 6 wherein the compression cone further comprises a hollow cone having walls gradually tapering to a rounded apex of the cone.

8. The invention of claim 7 wherein the compression cone is made of a material which is a radiolucent to x-rays.

9. The invention of claim 8 wherein the compression cone further comprises a marker made of a metallic material.

10. The invention of claim 1 wherein the hand and the wrist of the user are protected from x-rays by a lead glove and wherein the hand so protected can grip the handle and the wrist cuff extends over the wrist so protected.

11. The invention of claim 2 wherein the device further comprises;
    a planar surface of the lever arm and the handle and;
    a thumb rest rib comprising an elongated protrusion extending substantially perpendicularly from the planar surface.

12. The invention of claim 11 wherein the device further comprises;
    a planar surface of the lever arm, wrist cuff and handle and;
    a reinforcing rib comprising an elongated protrusion on the planar surface.

13. The invention of claim 12 wherein the wrist cuff further comprises a hook end at the end of the wrist cuff not adjacent to the lever arm.

14. The invention of claim 13 wherein the device is a body compression device and the work element is a compression cone.

15. The invention of claim 14 wherein the compression cone further comprises a hollow cone having walls gradually tapering to a rounded apex of the cone.

16. The invention of claim 15 wherein the compression cone is made of a material which is radiolucent to x-rays.

17. The invention of claim 16 wherein the compression cone further comprises a marker made of a metallic material.

18. The invention of claim 17 wherein the hand and the wrist of the user are protected from x-rays by a lead glove and wherein the hand so protected can grip the handle and the wrist cuff extends over the wrist so protected.

* * * * *